(12) United States Patent
Jezek

(10) Patent No.: US 9,005,611 B2
(45) Date of Patent: *Apr. 14, 2015

(54) PROTEIN FORMULATION

(75) Inventor: Jan Jezek, Wellingborough (GB)

(73) Assignee: Arecor Limited, Cambridge (GB)

( * ) Notice: Subject to any disclaimer, the term of this patent is extended or adjusted under 35 U.S.C. 154(b) by 227 days.

This patent is subject to a terminal disclaimer.

(21) Appl. No.: 12/913,857

(22) Filed: Oct. 28, 2010

(65) Prior Publication Data

US 2011/0097348 A1    Apr. 28, 2011

Related U.S. Application Data

(63) Continuation of application No. PCT/GB2009/050457, filed on May 1, 2009.

(30) Foreign Application Priority Data

May 1, 2008 (GB) .................................. 0807929.5
Feb. 13, 2009 (GB) .................................. 0902472.0

(51) Int. Cl.
- A61K 39/395 (2006.01)
- C07K 14/00 (2006.01)
- A61K 9/00 (2006.01)
- A61K 47/10 (2006.01)
- A61K 47/12 (2006.01)

(52) U.S. Cl.
CPC ............... *C07K 14/00* (2013.01); *A61K 9/0019* (2013.01); *A61K 47/10* (2013.01); *A61K 47/12* (2013.01)

(58) Field of Classification Search
None
See application file for complete search history.

(56) References Cited

U.S. PATENT DOCUMENTS

| | | | |
|---|---|---|---|
| 3,051,627 A | 8/1962 | Bradford et al. | |
| 2003/0199076 A1 | 10/2003 | Kuroita et al. | |
| 2005/0031549 A1 | 2/2005 | Quay et al. | |
| 2005/0272657 A1 | 12/2005 | O' Connor et al. | |
| 2007/0134199 A1 | 6/2007 | Frevert | |
| 2008/0161237 A1* | 7/2008 | Bacher et al. .................. | 514/12 |
| 2009/0136538 A1 | 5/2009 | Jezek | |
| 2009/0148406 A1 | 6/2009 | Jezek | |
| 2010/0028372 A1 | 2/2010 | Jezek | |
| 2011/0033549 A1 | 2/2011 | Jezek | |
| 2011/0034898 A1 | 2/2011 | Jezek | |

FOREIGN PATENT DOCUMENTS

| | | |
|---|---|---|
| EP | 0 009 222 A2 | 4/1980 |
| EP | 0 072 581 A1 | 2/1983 |
| EP | 0 513 914 | 11/1992 |
| EP | 0 884 053 A1 | 12/1998 |
| EP | 0 909 564 A1 | 4/1999 |
| EP | 0 938 902 A1 | 9/1999 |
| EP | 0 948 358 | 10/1999 |
| EP | 1 314 437 A1 | 5/2003 |
| EP | 1 506 786 A1 | 2/2005 |
| GB | 2 188 419 | 9/1987 |
| JP | 11-222441 | 8/1999 |
| WO | 9828007 A1 | 7/1998 |
| WO | 00/47224 A2 | 8/2000 |
| WO | 03/009869 A1 | 2/2003 |
| WO | 03/021258 A1 | 3/2003 |
| WO | 03/066681 A1 | 8/2003 |
| WO | 2004019861 A2 | 3/2004 |
| WO | 2005/007185 A2 | 1/2005 |
| WO | WO 2005/089794 A2 | 9/2005 |
| WO | 2008066322 A1 | 6/2008 |

OTHER PUBLICATIONS

Wang, International J. of Pharmaceutics, vol. 289, p. 1-30, 2005.*
U.S. Appl. No. 12/913,838, Jezek, co-pending application.
Sokhey, J., et al., "Stability of Oral Polio Vaccine at Different Temperatures," Vaccine, 6(1): 12-13 (1988).
Ralph, J. P., et al., "Size-Exclusion Chromatography of Solubilised Low-Rank Coal," The Journal of Chromatography, 724(1-2): 97-105 (1996).
Majhi, P. R., et al., "Electrostatically Driven Protein Aggregation: β-Lactoglobulin at Low Ionic Strength," Langmuir, 22 (22): 9150-9159 (2006).
Berghofer, V. E., et al., "Untersuchung gefriergetrockneter Stärkekleister and Stärkeschwämme im Rasterelektronenmikroskop," Starch, 28(4): 113-121 (1976) (English abstract on p. 1).
Antosiewicz. J., et al., "Prediction of pH-dependent Properties of Proteins," J. Mol. Biol., 238: 415-436 (1994).
Elcock, A. H., "Realistic Modeling of the Denatured States of Proteins Allows Accurate Calculations of the pH Dependence of Protein Stability," J. Mol. Biol., 294: 1051-1062 (1999).
Remmele, et al., "Interleukin-1 Receptor (IL-1R) Liquid Formulation Development Using Differential Scanning Calorimetry," Pharmaceutical Research, 15(2): 200-208 (1998).
Alexov, E., "Numerical calculations of the pH of maximal protein stability. The effect of the sequence composition and three-dimensional structure," Eur. J. Biochem., 271(1), 173-185 (2004).
Nelson, D. I., et al., Eds., Lehninger Principles of Biochemistry, 3rd Edition, Worth Publishers, p. 118 (2000).

(Continued)

*Primary Examiner* — Yunsoo Kim

(74) *Attorney, Agent, or Firm* — Sterne, Kessler, Goldstein & Fox P.L.L.C.

(57) ABSTRACT

A composition comprises a biological molecule that is susceptible to aggregation, dimerization or hydrolysis, wherein the ionic strength is less than 40 mM.

39 Claims, No Drawings

(56) References Cited

OTHER PUBLICATIONS

Berti, Francesco, et al., "Water Accessibility, Aggregation, and Motional Features of Polysaccharide-Protein Conjugate Vaccines," *Biophysical Journal* 86:3-9, Biophysical Society, United States (2004).

European Search Report for EP Application No. 12157010.5-1219, European Patent Office, Netherlands, mailed on May 29, 2012.

* cited by examiner

PROTEIN FORMULATION

RELATED APPLICATIONS

This application is a continuation of International Application No. PCT/GB2009/050457, which designated the United States and was filed on May 1, 2009, published in English. This application claims priority under 35 U.S.C. §119 or 365 to United Kingdom Application No.'s 0807929.5, filed on May 1, 2008 and 0902472.0, filed on Feb. 13, 2009. The entire teachings of the above applications are incorporated herein by reference.

FIELD OF THE INVENTION

This invention relates to the stability of a wide range of molecules. In particular, the invention relates to the stability of proteins and other biological molecules which exhibit formation of dimers or higher molecular weight species. The invention also relates to the stability of a wide range of molecules, ranging from small molecules to complex supramolecular systems, in particular to the stability of such molecules wherein a hydrolysis of a bond between two conjugated parts of the molecule or the system is a problem. The invention relates to stability of molecules in aqueous systems, for example in an aqueous solution, in aqueous gel form or in non-liquid state such as solid state where free or bound water is present e.g. in frozen condition or following partial removal of water such as by drying or freeze-drying.

BACKGROUND OF THE INVENTION

Many biological molecules, such as proteins, are unstable and are susceptible to structural degradation and consequent loss of activity while stored, particularly in aqueous solutions. The processes involved in protein degradation can be divided into physical (i.e. processes based on non-covalent interactions, such as loss of quaternary, tertiary or secondary structure, aggregation, surface adsorption) and chemical (i.e. processes involving a covalent change such as de-amidation, hydrolysis, oxidation, disulphide scrambling etc.). The rates of the degradation processes are typically proportional to temperature. Proteins are therefore generally more stable at lower temperatures. The same degradation principles generally apply to other biological molecules and more complex supramolecular systems made up of a discrete number of assembled molecular subunits or components.

Both physical and chemical instability of molecules is a particular problem in many applications, such as applications intended for therapy.

One particular stability problem of proteins and other biological molecules, especially those used in therapy, is formation of dimers or higher molecular weight species (HMWS), whereby two or more molecules aggregate and form larger molecular weight entities. Such aggregation can be either reversible or irreversible, depending on the nature of the interactions between the protein molecules. A number of different types of non-covalent interactions can be engaged in protein aggregation, such as ionic interactions between positively and negatively charged parts of the protein molecules, or hydrophobic interactions between hydrophobic patches at the protein surface. In rare cases, even covalent interactions such as disulphide bonds can facilitate protein aggregation. Whilst the different types of interactions can combine, it is typical that one particular type is the dominant force in the process of HMWS formation. So, for example, some proteins can form HMWS predominantly due to ionic interactions, while other proteins mainly due to hydrophobic interactions. The conditions that drive the formation of HMWS forward vary depending on the dominant interactions involved. Consequently, different conditions can be employed to minimise the rate of HMWS formation of different proteins.

Formation of HMWS can be measured by various techniques such as size-exclusion chromatography. Formation of large aggregates can be followed by various light-scattering techniques or microscopic or visual assessment.

Aggregation is a particular problem in formulations of therapeutic biological molecules. Although the aggregated forms, especially if reversible, are often equipotent with the native form of the protein, formation of HMWS represents a considerable hurdle in the regulatory approval process Another particular stability problem of many different classes of molecules, ranging from small molecules to complex supramolecular systems, is cleavage of a bond between two conjugated parts of the molecule or the system. Examples of such undesirable processes include cleavage of a polysaccharide moiety from a carrier protein in a number of polysaccharide-based vaccines (e.g. *Haemophillus influenzae* b vaccine) or a cleavage between key domains of fusion proteins (e.g. Etanercept). Acid or base hydrolysis is typically the mechanism of such degradation processes.

Hydrolysis is a chemical reaction during which a water molecule is split into hydrogen and hydroxide ions which go on to participate in cleavage of a particular covalent bond. Hydrolysis requires the presence of water and is known to be a pH-dependent process. However, proton transfer from molecules can also be involved in the mechanism of hydrolytic cleavage.

SUMMARY OF THE INVENTION

The present invention is based on the discovery of several desirable parameters of aqueous formulations of small molecules, macromolecules such as proteins and supramolecular systems. Application of the invention results in an improvement of stability, potentially substantial, of such molecules or systems. In some aspects, application of the invention results in desirable reduction of formation of dimers and HMWS during storage. In other aspects, application of the invention results in desirable reduction of the rate of destabilising hydrolytic processes.

DESCRIPTION OF THE INVENTION

The term "small molecule" is used herein to encompass a molecule of any chemical structure with a molecular weight between 50-2000 Da.

The term "macromolecule" is used herein to encompass a molecule of any chemical structure with a molecular weight higher than 2000 Da. Macromolecules will typically be of polymeric nature, but the invention is not limited to the polymeric macromolecules.

The term "protein" is used herein to encompass molecules or molecular complexes consisting of a single polypeptide, molecules or molecular complexes comprising two or more polypeptides and molecules or molecular complexes comprising one or more polypeptides together with one or more non-polypeptide moieties such as prosthetic groups, cofactors etc. The term "polypeptide" is intended to encompass polypeptides comprising covalently linked non-amino acid moieties such as glycosylated polypeptides, lipoproteins etc.

The term "supramolecular systems" is used herein to encompass any system made up of a discrete number of assembled molecular subunits or components.

The term "substance used in therapy" is used herein to encompass any substance which is developed with the intention to be used in clinical trials or to be approved as part of a medical device or as a drug product.

The term "high molecular weight species" is used herein to encompass any species formed by aggregation of the native form of a species, such as a protein. The term encompasses both soluble and insoluble aggregated forms.

The term "displaced buffer" is used herein to encompass any additive present in a composition of specified pH which is capable of exchanging protons and has $pK_a$ value(s) at least 1 unit more or less than the pH of the composition at the intended temperature range of storage of the composition. The art of applying displaced buffers to formulations of biologicals is described in WO2008/084237, the content of which is incorporated herein by reference. In that specification, the importance of, and the distinction between, conventional and displaced buffers is described.

The term "ionic strength" is used herein as the following function of the concentration of all ions in a solution:

$$I = \sum_{X=1}^{n} c_x z_x^2$$

where $C_x$ is molar concentration of ion x (mol L$^{-1}$), $Z_x$ is the absolute value of the charge of ion x. The sum covers all ions (n) present in the solution.

Many proteins and other biological molecules undergo the process of aggregation, i.e. the formation of HMWS, during storage, especially in aqueous solutions. Aggregation is typically facilitated by non-covalent interactions such as charge-charge interactions or hydrophobic interactions between amino acid residues at the surface of individual protein molecules. Both the charge and the hydrophobicity of amino acid side chains are pH dependent. For example, histidine residue ($pK_a$ about 6.1) exists predominantly in the charged form at pH<6.1 and predominantly in the uncharged form at pH>6.1, the uncharged form being considerably more hydrophobic than the charged one. Consequently, the tendency of proteins and other biological molecules to aggregate is also dependent on pH. It is therefore important to optimise the pH of the formulation in order to minimise the tendency of the protein to form dimers or HMWS. However, apart from pH there are other parameters that are also very important for minimising the tendency of proteins and other biological molecules to aggregate. Such parameters may vary considerably depending on the nature of the aggregation process. The present invention addresses such parameters. The importance of such parameters may be relatively low if the protein is maintained at optimal pH with respect to aggregation, but is very significant if the protein must be maintained at a pH away from the optimum, for example for reasons of regulatory acceptability or for improved solubility.

A preferred feature of the present invention in relation to reducing the rate of HMWS formation of proteins and other biological molecules is in combining the following formulation features in the formulation of a protein or other biological molecules or supramolecular systems:
  Minimal ionic strength: ionic strength of the formulation is kept minimal, such as less than 40 mM, preferably less than 20 mM, most preferably less than 10 mM.
  Use of a charged species which comprises a considerable non-polar (hydrophobic) region such as a benzene nucleus or an aliphatic chain of four or more carbon atoms. The preferred example of such amphiphilic compound that can be usefully employed in the protein compositions according to the present invention is benzoic acid, particularly its ionic form (benzoate ion).
  Optionally, the use of displaced buffers to maintain the required pH: the formulation is substantially free of a conventional buffer, i.e a compound with $pK_a$ within 1 unit of the pH of the composition at the intended temperature range of storage of the composition, and comprises one or more additives (displaced buffers) which are capable of exchanging protons with the biological molecule and have $pK_a$ values at least 1 unit more or less than the pH of the composition at the intended temperature range of storage of the composition; the art of applying displaced buffers to formulations of biologicals is described in PCT/BG2007/000082.

By combining these formulation parameters, the rate of the undesirable HMWS formation can be reduced substantially. Preferably, the formulation is kept at a pH at which the rate of HMWS formation is minimal. Optimal pH can be established experimentally. However, the invention is applicable at pH away for such pH optimum.

The invention is particularly applicable to stabilising substances used in therapy.

The formation of dimers or HMWS is very likely to involve hydrophobic interactions. It means that hydrophobic regions at the surface of two or more protein molecules interact and engage in non-covalent binding interactions. This leads to gradual aggregation. Without wishing to be bound by theory, it is useful to realise that the formation of hydrophobic bonds is known to be thermodynamically driven by increase in entropy of the system by eliminating unfavourable interactions between the hydrophobic regions and the surrounding aqueous environment. Importantly, the increase in entropy will be even higher if there is a high concentration of charged species present in the aqueous environment. For this reason, the formation of HMWS, if facilitated mainly by hydrophobic interactions, is likely to proceed more readily at high ionic strength than at low ionic strength. This is particularly the case if the protein is not kept at an optimal pH with respect to minimal aggregation.

A typical formulation of a therapeutic protein or other biological molecule contains a buffer (for example phosphate, histidine or citrate) and one or more of the following excipients: tonicity modifiers (for example inorganic salts or amino acids), surfactants (for example Polysorbate 80) and sugars or polyalcohols (for example sucrose or mannitol). Many of these buffers and excipients contribute considerably to the ionic strength of the aqueous formulation, so the compositions of proteins intended for therapy are typically of relatively high ionic strength, such as higher than 100 mM, higher than 150 mM or higher than 200 mM. It is believed that the importance of low ionic strength in minimisation of protein aggregation, especially if the protein is maintained outside the optimum pH with respect to aggregation, has not been appreciated, particularly in commercial formulations of therapeutic proteins.

Therefore, in one aspect, the present invention discloses a method for minimisation of dimer formation or formation of HMWS of a protein or other biological molecules, particularly of such molecules used in therapy, by putting the protein in a formulation of certain pH with minimal ionic strength, such as less than 30 mM, preferably less than 15 mM, most preferably less than 10 mM. Such method is particularly useful if the protein is maintained outside the optimum pH with respect to aggregation, for example for reasons of improved solubility.

In another aspect of the present invention, an aqueous composition comprises a protein or other biological molecule at a pH adjusted to a particular value, with reduced rate of dimer formation or formation of HMWS at such pH, further characterised in that the ionic strength of the composition is less than 30 mM, preferably less than 15 mM, most preferably less than 10 mM. The osmolarity of such composition can be adjusted to a required level using non-ionic species such as sugars or sugar alcohols.

Some concentration of ionic species is typically needed as buffers in a formulation of a therapeutic protein. Therefore, the present invention may pose problems in ensuring sufficient buffering capacity whilst minimising the rate of aggregation. Such problems may be addressed by a specific choice of ionic species as buffers as follows: Since the ionic strength of an ionic species is proportional to the square of the charge of such species multivalent ions contribute considerably more strongly to ionic strength than monovalent ones. The use of monovalent ions as buffers is therefore preferable over the multivalent ones to ensure a degree of buffering capacity while minimising the ionic strength of the composition.

Therefore, in another aspect of the present invention an aqueous composition comprises a protein or other biological molecule at a pH adjusted to a particular value, with reduced rate of dimer formation or formation of HMWS at such pH, further characterised in that the composition is substantially free of multivalent ions and the ionic strength of the composition is less than 30 mM, preferably less than 15 mM, most preferably less than 10 mM. The osmolarity of such composition can be adjusted to a required level using non-ionic species such as sugars or sugar alcohols.

It has been shown experimentally that it is beneficial if at least one of the charged species in such protein compositions comprises a considerable non-polar (hydrophobic) region such as a benzene nucleus or an aliphatic chain of four or more carbon atoms. The use of such amphiphilic compound further reduces the rate of dimer formation or formation of HMWS. The preferred example of such amphiphilic compound that can be usefully employed in the protein compositions according to the present invention is benzoic acid, particularly its ionic form (benzoate ion). Benzoic acid comprises one carboxylic group, which is predominantly charged at pH>4.2, and a non-polar benzene nucleus. It is also an approved excipient in therapeutic formulations. Without wishing to be bound by theory, it is believed that the beneficial effect of benzoic acid and similar type of excipients is due to its binding to the hydrophobic regions of the protein via the benzene nucleus while exposing the charge to the aqueous solution. Thus a charge is introduced to the hydrophobic region of the protein, which lowers the tendency of the hydrophobic region to engage in hydrophobic interactions. This results in lower rate of protein aggregation.

Therefore, in another aspect of the present invention an aqueous system comprises a protein or other biological molecule at a pH adjusted to a particular value, with reduced rate of dimer formation or formation of HMWS at such pH, further characterised in that (i) the ionic strength of the composition is less than 30 mM, preferably less than 15 mM, most preferably less than 10 mM, and (ii) the composition comprises a charged compound which contains an extensive hydrophobic region such as a benzene nucleus or an aliphatic chain of four or more carbon atoms. Benzoate ion is the preferred excipient in such composition. The osmolarity of such composition can be adjusted to a required level using uncharged species such as sugars or sugar alcohols.

In another aspect, the present invention discloses a method for minimisation of dimer formation or formation of HMWS of a protein or other biological molecule by (i) putting the protein in a formulation of certain pH with minimal ionic strength, such as less than 30 mM, preferably less than 15 mM, most preferably less than 10 mM, and (ii) adding to the composition an ionic compound which contains an extensive hydrophobic region such as a benzene nucleus or an aliphatic chain of four or more carbon atoms. Such method is particularly useful if the protein is maintained outside the optimum pH with respect to aggregation, for example for reasons of improved solubility.

In addition to improving stability of biological molecules by reduced formation of HMWS, the present invention also addresses the stability of therapeutic molecules by reducing the rate of hydrolytic processes, such as cleavage of amide bonds or ester bonds.

Hydrolysis is a particular stability problem of many different classes of molecules, ranging from small molecules to complex supramolecular systems. Examples of such undesirable processes include cleavage of a polysaccharide moiety from a carrier protein in a number of polysaccharide-based vaccines (e.g. *Haemophillus influenzae* b vaccine) or a cleavage between key domains of fusion proteins (e.g. Etanercept). Acid or base hydrolysis is typically the mechanism of such degradation processes.

Hydrolysis can also be part of the mechanism of more complex processes, such as deamidation of asparagine or aspartate isomerisation. The present invention is therefore also applicable in stabilising various molecules with respect to such processes which comprise hydrolysis as part of their molecular mechanism.

Hydrolysis is a chemical reaction during which water molecule is split into hydrogen and hydroxide ions which go on to participate in cleavage of a particular covalent bond. Hydrolysis is known to be a very pH dependent process. However, proton transfer from molecules other than water can also be involved in the mechanism of hydrolytical cleavage. Hydrolysis is generally known to be strongly dependent on pH. Optimization of pH is therefore essential in order to reduce the rate of hydrolysis. However, other formulation parameters can bring about further reduction in the rate of hydrolysis. The present invention addresses additional key formulation parameters that can be applied to reduce further the rate of hydrolytic processes in formulations of a wide range of molecules and more complex systems.

Another preferred feature of the present invention in relation to reducing the rate of hydrolysis is in combining the following formulation features in the formulation of a particular molecule or a more complex system:

Minimal ionic strength: ionic strength of the formulation is kept minimal, such as less than 40 mM, preferably less than 20 mM, most preferably less than 10 mM.

Use of displaced buffers to maintain the required pH: the formulation is substantially free of a conventional buffer, i.e a compound with $pK_a$ within 1 unit of the pH of the composition at the intended temperature range of storage of the composition, and comprises one or more additives (displaced buffers) which are capable of exchanging protons with other molecules and have $pK_a$ values at least 1 unit more or less than the pH of the composition at the intended temperature range of storage of the composition; the art of applying displaced buffers to formulations of biologicals is described in WO2008/084237.

By combining these formulation parameters, the rate of the undesirable hydrolytic process can be reduced substantially. Preferably, the formulation is kept at a pH at which the rate of hydrolysis is minimal. Optimal pH can be established experimentally. However, the invention is applicable at pH away for such pH optimum.

The invention is particularly applicable to stabilising substances used in therapy.

In one aspect, the present invention discloses a method for minimisation of the rate of hydrolytic process on a molecule or supramolecular system by putting the molecule or the system in a formulation of certain pH with minimal ionic strength, such as less than 40 mM, preferably less than 20 mM, most preferably less than 10 mM. Preferably, the pH of the composition is adjusted to a level at which the rate of the undesirable hydrolytic process is minimal.

In another aspect of the present invention, an aqueous composition comprises a molecule or a supramolecular system, at a pH adjusted to a particular value, further characterised in that the ionic strength of the composition is less than 40 mM, preferably less than 20 mM, most preferably less than 10 mM. The osmolarity of such composition can be adjusted to a required level using non-ionic species such as sugars or sugar alcohols. Preferably, the pH of the composition is adjusted to a level at which the rate of the undesirable hydrolytic process is minimal.

Some concentration of ionic species is typically needed as buffers or antioxidants in a formulation of a therapeutic protein. Therefore, the present invention may pose problems in ensuring sufficient buffering capacity whilst minimising the rate of hydrolysis. Such problems may be addressed by the use of monovalent ions as buffers or antioxidants while avoiding multivalent ones to ensure a degree of buffering capacity while minimising the ionic strength of the composition. Therefore, in another aspect of the present invention an aqueous composition comprises a molecule or a supramolecular system, at a pH adjusted to a particular value, further characterised in that the composition is substantially free of multivalent ions and the ionic strength of the composition is less than 40 mM, preferably less than 20 mM, most preferably less than 10 mM. The osmolarity of such composition can be adjusted to a required level using non-ionic species such as sugars or sugar alcohols. Preferably, the pH of the composition is adjusted to a level at which the rate of the undesirable hydrolytic process is minimal.

It was shown experimentally that in order to reduce further the rate of hydrolysis it is beneficial to use displaced buffers while keeping the composition substantially free of conventional buffers. Therefore, in another aspect of the present invention an aqueous composition comprises a molecule or supramolecular system, at a pH adjusted to a particular value, further characterised in that the composition is substantially free of conventional buffer and comprises one or more additives which are capable of exchanging protons with the protein and have $pK_a$ values at least 1 unit more or less than the pH of the composition at the intended temperature range of storage of the composition; the ionic strength of the composition is less than 40 mM, preferably less than 20 mM, most preferably less than 10 mM. The osmolarity of such composition can be adjusted to a required level using non-ionic species such as sugars or sugar alcohols. Preferably, the pH of the composition is adjusted to a level at which the rate of the undesirable hydrolytic process is minimal.

Various hydrolytic processes are catalysed by proton transfer at the cleavage site facilitated by molecules other than water, for example molecules of buffers. Without wishing to be bound by theory, it is believed that the benefit of using displaced buffers instead of conventional buffers in compositions of molecules that are prone to hydrolytic cleavage is in minimising the rate of proton transfer from molecules of conventional buffers to or from the cleavage site.

The invention is illustrated by the following Examples:

Example 1

Formation of HMWS was followed in a solution of alpha-glucosidase (12.5 mg/mL) using the following size-exclusion chromatographic method: The mobile phase was 25 mM sodium phosphate (pH 6.2) containing 150 mM NaCl. The mobile phase was filtered prior to its use. The liquid chromatograph (Agilent 1100 series) was equipped with a 214 nm detector, guard column and a 7.8×300 mm BioSep SEC-S2000 column. The flow rate was maintained at 0.45 mL/min. 20 μL of aqueous samples of alpha-glucosidase were injected. The level of high molecular weight species was expressed as the percentage of the total peak area of all peaks with elution time shorter than that of the main peak versus the area of the main peak.

The aggregation rate was studied at 25° C. in the presence of 4 mM TRIS buffer. The buffering strength of TRIS buffer at pH<6.5 is minimal, but sufficient buffering capacity originated from the relatively concentrated enzyme itself at such pH. The optimum pH with respect to minimal formation of HMWS was found to be around 6.5. The aggregation rate was higher both at lower and at higher pH. Increase in ionic strength resulted in considerable increase in the rate of HMWS, especially outside the optimum pH (Table 1). So, whilst the increase in ionic strength resulted only in moderate increase of the aggregation rate at ph 6.5 the increase was considerably higher both at higher and at lower pH.

TABLE 1

Formation of HMWS (%) at 25° C. (3 weeks) in aqueous formulation of alpha-glucosidase (12.5 mg/mL) in the presence of 4 mM TRIS buffer and the indicated concentration of NaCl.

| pH | 0 mM NaCl | 25 mM NaCl | 100 mM NaCl |
|---|---|---|---|
| 5.5 | 4.13 | 9.94 | 34.68 |
| 6.0 | 1.07 | 3.12 | 8.92 |
| 6.5 | 0.44 | 1.36 | 3.26 |
| 7.0 | 1.06 | 4.80 | 5.11 |
| 7.5 | 4.36 | 7.99 | 22.68 |
| 8.0 | 10.01 | 32.32 | 45.96 |

Example 2

Effect of benzoic acid was studied on the rate of HMWS formation at 25° C. and 40° C. (2 weeks) in a solution of alpha-glucosidase (12.5 mg/mL) using the size-exclusion chromatographic method described in Example 1. The aggregation rate was studied in the presence of 2 mM TRIS buffer. Apart from benzoic acid and/or TRIS, no other charged species were present in the formulation.

The presence of benzoic acid was shown to reduce the rate of formation of HMWS both at 25° C. (Table 2) and at 40° C. The effect was more marked at pH 7.5, i.e. away from the pH optimum with respect to minimal aggregation, than at the pH optimum (pH 6.5)

TABLE 2

Formation of HMWS (%) at 25° C. (4 weeks) in
aqueous formulation of alpha-glucosidase (12.5 mg/mL)
in the presence of TRIS buffer (2 mM) either in the
presence or in the absence of benzoic acid (2 mM).

| pH  | Without 2 mM benzoic acid | With 2 mM benzoic acid |
|-----|---------------------------|------------------------|
| 6.5 | 1.93                      | 0.92                   |
| 7.0 | 2.23                      | 0.83                   |
| 7.5 | 2.40                      | 0.98                   |

TABLE 3

Formation of HMWS (%) at 40° C. (2 weeks) in
aqueous formulation of alpha-glucosidase (12.5 mg/mL)
in the presence of TRIS buffer (2 mM) either in the
presence or in the absence of benzoic acid (2 mM).

| pH  | Without 2 mM benzoic acid | With 2 mM benzoic acid |
|-----|---------------------------|------------------------|
| 6.5 | 16.82                     | 3.76                   |
| 7.0 | 18.16                     | 3.80                   |
| 7.5 | 25.09                     | 4.08                   |

Example 3

Hydrolysis of the polysaccharide antigen (polyribose-phosphate-ribose, PRP) from a carrier protein is a particular problem of the *Haemophillus influenzae* b (Hib) vaccine. The extent of the hydrolysis can be expressed in terms of the percentage of the free (i.e. unbound to the carrier protein) PRP in the formulation. The method is based on separation of free PRP from bound PRP and subsequent quantification of PRP in both fractions by the Bial reaction (Kabat E A, Mayer M: Carbohydrate estimation. In: Experimental immunochemistry. Springfield, Ill.: C Thomas, 1961. p. 526-37). In the experiment described here the free PRP was separated from the bound PRP by precipitating Hib vaccine with deoxycholate. Digestion and analysis with orcinol dye was then carried out in order to determine the portion of ribose present in each fraction. The following procedure was followed: Neat sample (200 µl; at 50 µg/ml) was pipetted in to a microcentrifuge tube. For the blank, 200 µl analytical water was used. To each tube 80 µl deoxycholate (0.1% w/v) was added and then vortexed. These were then incubated (30 mins, at +4° C.). After this incubation, hydrochloric acid (50 µl, 1M) was added to each tube. All tubes were vortexed and then centrifuged (45 mins at 5.2 g) at +4° C. While in the cold room in each case 165 µl of supernatant was removed, and put in to a microfuge tube. The rest of the supernatant was then removed and discarded. The volume of each supernatant was made up to 200 µl with the addition of analytical water (35 µl). The supernatants were now ready for the analysis of free ribose. At room temperature, sodium hydroxide (0.1M, 200 µl) was added to each pellet. The pellet was vortexed and agitated using a pipette to dissolve it. In each case half the pellet solution (100 µl) was aliquoted in to a new microfuge tube and the volume made up to 200 µl with analytical water (100 µl). The pellet solutions were now ready for analysis of ribose bound to glycoprotein. In the fume cupboard and wearing gloves, to both the supernatants and the pellet solutions add 200 µl ferric chloride in 10 M hydrochloric acid. Then in each case 20 µl orcinol dye (10% in absolute ethanol) solution was added in the mixture incubated at 95° C. for 40 min. Immediately after incubation the tubes were cooled in a beaker of cold water (+4° C.). The contents were transferred to cuvettes and the absorbance at 670 nm was measured. The values obtained must have the appropriate blank values subtracted. Supernatants will take off the supernatant blank and the pellet values will take off the pellet blanks (this difference is due to the presence of deoxycholate in the pellet samples, which affects the absorbance value). Resulting value can then be used in the following equation:

% Free ribose=(Absorbance-supernatant)/(Absorbance-supernatant+Absorbance-pellet)×100

A number of commercially available Hib vaccine products (for example HibTITER, Wyeth) are currently formulated in 0.9% saline as the key formulation ingredient. It was shown that a significant improvement in stability can be achieved if the vaccine is formulated in a low ionic strength environment at pH around 6. Histidine was used a buffer in this case and uncharged 1,2-propanediol was used as tonicity modifier. Stability was studied at 40° C. More than 20% increase of free PRP can be observed in the currently marketed formulation (saline, pH~6) of Hib vaccine after 3 weeks and >60% after 13 weeks of incubation at 40° C. In contrast, only 11% increase on free PRP could be observed after 3 weeks and 40% after 13 weeks of incubation at 40° C. in the low ionic strength histidine-based formulation. However, the best stability could be achieved if the histidine buffer of the low-ionic strength formulation was replaced by a displaced buffer based on combination of Tris(aminomethyl)hydroxymethane (10 mM) and sodium lactate (10 mM). Less than 5% increase of free PRP can be observed in such formulation after incubation at 40° C. for 3 weeks and <25% after incubation at 40° C. for 13 weeks.

The invention claimed is:
1. An aqueous composition comprising a protein used in therapy wherein:
   (a) the composition has a pH at which the protein is susceptible to aggregation or dimerization;
   (b) the composition comprises an amphiphilic excipient that has a charged region and a non-polar region, wherein the non-polar region is a benzene nucleus; and
   (c) the ionic strength of the composition in the absence of the protein is less than 30 mM when calculated using the formula

$$I = \sum_{x=1}^{n} c_x z_x^2$$

in which $C_x$ is molar concentration of ion x (mol L$^{-1}$), $Z_x$ is the absolute value of the charge of ion x and the sum covers all ions (n) present in the composition.

2. An aqueous composition according to claim 1, wherein the ionic strength is less than 20 mM.

3. An aqueous composition according to claim 1, which is substantially free of divalent ions.

4. An aqueous composition according to claim 1, wherein the amphiphilic excipient is benzoate ion.

5. An aqueous composition according to claim 1, which is substantially free of a buffer with a pKa within 1 unit of the pH of the composition and comprises one or more displaced buffers which have pKa values at least 1 unit more or less than the pH of the composition.

6. An aqueous composition according to claim 5, which has the displaced buffer tris(hydroxymethyl)aminomethane.

7. An aqueous composition according to claim 5, which has the displaced buffer benzoic acid.

8. An aqueous composition according to claim 5, which has the displaced buffer lactate anion.

9. An aqueous composition according to claim 5, which has the displaced buffers tris(hydroxymethyl)aminomethane and benzoate ion or lactate anion.

10. An aqueous composition according to claim 1, wherein the protein is a vaccine.

11. An aqueous composition according to claim 1, which further comprises a sugar or sugar alcohol.

12. An aqueous composition according to claim 1, which further comprises a physiologically acceptable chelating agent.

13. An aqueous composition according to claim 1, which further comprises a physiologically acceptable detergent.

14. An aqueous composition according to claim 1, which is a therapeutic formulation.

15. An aqueous composition comprising a protein used in therapy wherein:
   (a) the composition has a pH at which the protein is susceptible to hydrolysis;
   (b) the composition is substantially free of a buffer with a pKa within 1 unit of the pH of the composition and comprises more than one displaced buffers which have a pKa value at least 1 unit more or less than the pH of the composition; and
   (c) the ionic strength of the composition in the absence of the protein is less than 40 mM when calculated using the formula $$I = \sum_{X=1}^{n} c_x z_x^2$$

in which $C_x$ is molar concentration of ion x (mol L$^1$), $Z_x$ is the absolute value of the charge of ion x and the sum covers all ions (n) present in the composition.

16. An aqueous composition according to claim 15, which is a polysaccharide based vaccine.

17. An aqueous composition according to claim 16, wherein the polysaccharide based vaccine is susceptible to cleavage of a polysaccharide moiety from a carrier protein.

18. An aqueous composition to claim 16, wherein said polysaccharide based vaccine is *Haemophilus influenza* b vaccine.

19. An aqueous composition according to claim 15, wherein the ionic strength is less than 30 mM.

20. An aqueous composition according to claim 15, wherein the ionic strength is less than 20 mM.

21. An aqueous composition according to claim 15, which is substantially free of divalent ions.

22. An aqueous composition according to claim 15, which further comprises an amphiphilic excipient that has a charged region and a non-polar region, wherein the non-polar region is a benzene nucleus.

23. An aqueous composition according to claim 22, wherein the amphiphilic excipient is benzoate ion.

24. An aqueous composition according to claim 15, which further comprises non-ionic species to adjust osmolarity.

25. An aqueous composition according to claim 15, which further comprises a sugar or sugar alcohol.

26. An aqueous composition according to claim 15, which further comprises a physiologically acceptable chelating agent.

27. An aqueous composition according to claim 15, which further comprises a physiologically acceptable detergent.

28. An aqueous composition according to claim 15, which is a therapeutic formulation.

29. An aqueous composition comprising a polysaccharide based vaccine wherein:
   (a) the composition has a pH at which the vaccine is susceptible to cleavage of a polysaccharide moiety from a carrier protein;
   (b) a buffer; and
   (c) wherein the ionic strength of the composition in the absence of the vaccine is less than 20 mM when calculated using the formula $$I = \sum_{X=1}^{n} c_x z_x^2$$

in which $C_x$ is molar concentration of ion x (mol L$^-$), $Z_x$ is the absolute value of the charge of ion x and the sum covers all ions (n) present in the composition.

30. An aqueous composition according to claim 29, wherein said polysaccharide based vaccine is *Haemophilus influenza* b vaccine.

31. An aqueous composition according to claim 29, which is substantially free of divalent ions.

32. An aqueous composition according to claim 29, which further comprises an amphiphilic excipient that has a charged region and a non-polar region, wherein the non-polar region is a benzene nucleus.

33. An aqueous composition according to claim 32, wherein the amphiphilic excipient is benzoate ion.

34. An aqueous composition according to claim 29, which is substantially free of a buffer with a pKa within 1 unit of the pH of the composition and comprises one or more displaced buffers which have pKa values at least 1 unit more or less than the pH of the composition.

35. An aqueous composition according to claim 29, which further comprises non-ionic species to adjust osmolarity.

36. An aqueous composition according to claim 29, which further comprises a sugar or sugar alcohol.

37. An aqueous composition according to claim 29, which further comprises a physiologically acceptable chelating agent.

38. An aqueous composition according to claim 29, which further comprises a physiologically acceptable detergent.

39. An aqueous composition according to claim 29, which is a therapeutic formulation.

\* \* \* \* \*

UNITED STATES PATENT AND TRADEMARK OFFICE
CERTIFICATE OF CORRECTION

| | | |
|---|---|---|
| PATENT NO. | : 9,005,611 B2 | Page 1 of 1 |
| APPLICATION NO. | : 12/913857 | |
| DATED | : April 14, 2015 | |
| INVENTOR(S) | : Jan Jezek | |

It is certified that error appears in the above-identified patent and that said Letters Patent is hereby corrected as shown below:

In the Claims

In column 12, line 17, claim 29(b), please replace "a buffer; and" with --the composition comprises a buffer; and--.

Signed and Sealed this
Fifteenth Day of September, 2015

Michelle K. Lee
*Director of the United States Patent and Trademark Office*